United States Patent
Fox et al.

(10) Patent No.: US 9,005,276 B2
(45) Date of Patent: Apr. 14, 2015

(54) BIOABSORBABLE STENT WITH PROHEALING LAYER

(71) Applicant: Abbott Cardiovascular Systems Inc., Santa Clara, CA (US)

(72) Inventors: William Jason Fox, Menlo Park, CA (US); Nathan Harold, San Jose, CA (US); Antonio Garcia, San Jose, CA (US); Andrew Tochterman, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 24 days.

(21) Appl. No.: 13/975,172

(22) Filed: Aug. 23, 2013

(65) Prior Publication Data

US 2013/0345795 A1    Dec. 26, 2013

Related U.S. Application Data

(63) Continuation of application No. 11/820,344, filed on Jun. 18, 2007, now Pat. No. 8,535,372.

(60) Provisional application No. 60/814,224, filed on Jun. 16, 2006.

(51) Int. Cl.
*A61F 2/86* (2013.01)
*A61F 2/06* (2013.01)

(52) U.S. Cl.
CPC .... *A61F 2/06* (2013.01); *A61F 2/86* (2013.01)

(58) Field of Classification Search
None
See application file for complete search history.

(56) References Cited

U.S. PATENT DOCUMENTS

| | | |
|---|---|---|
| 5,605,696 A | 2/1997 | Eury et al. |
| 2004/0098095 A1 | 5/2004 | Burnside et al. |
| 2004/0249445 A1 | 12/2004 | Rosenthal et al. |
| 2005/0004663 A1 | 1/2005 | Llanos et al. |
| 2005/0019404 A1 | 1/2005 | Sung et al. |
| 2005/0107870 A1 | 5/2005 | Wang et al. |
| 2005/0124976 A1 | 6/2005 | Devens et al. |
| 2005/0192662 A1 | 9/2005 | Ward |
| 2006/0136048 A1 | 6/2006 | Pacetti et al. |
| 2007/0128723 A1 | 6/2007 | Cottone et al. |
| 2009/0005860 A1 | 1/2009 | Gale et al. |

*Primary Examiner* — Allison Fox
(74) *Attorney, Agent, or Firm* — Squire Patton Boggs (US) LLP

(57) ABSTRACT

Stents and methods of fabricating stents with prohealing layers and drug-polymer layers are disclosed.

16 Claims, 3 Drawing Sheets

BIOABSORBABLE STENT WITH PROHEALING LAYER

CROSS REFERENCE TO RELATED APPLICATION

This application is a continuation of U.S. patent application Ser. No. 11/820,344 filed Jun. 18, 2007 which claims the benefit of U.S. Patent Application No. 60/814,224 which was filed on Jun. 16, 2006, both of which are incorporated by reference herein.

BACKGROUND OF THE INVENTION

1. Field of the Invention

This invention relates to stents and methods of fabricating bioabsorbable stents with a prohealing layer.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. The stent may be visualized during delivery and deployment using X-Ray fluoroscopy if it contains radiopaque materials.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent should be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

SUMMARY OF THE INVENTION

Various embodiments of the present invention include a stent comprising: a bioabsorbable prohealing layer configured to promote endothelialization upon exposure to bodily fluids; and a bioabsorbable drug-polymer layer above a luminal surface of the prohealing layer.

Further embodiments of the present invention include a method of fabricating a bioabsorbable stent, the method comprising: forming a bioabsorbable prohealing coating layer over a bioabsorbable base polymer tube, the prohealing coating layer configured to promote endothelialization upon exposure to bodily fluids; forming a bioabsorbable drug-polymer layer over the prohealing coating layer; and laser cutting a stent pattern in the coated polymer tube to form a stent.

DETAILED DESCRIPTION OF THE INVENTION

Various embodiments of the present invention include a stent formed from a bioabsorbable polymer(s) having a prohealing layer for promoting vascular healing and a therapeutic layer(s) for treating inflammation, neointimal cell proliferation, or both. The present invention is applicable to devices including, but is not limited to, self-expandable stents, balloon-expandable stents, stent-grafts, and generally expandable tubular devices for various bodily lumen.

Figure 1:
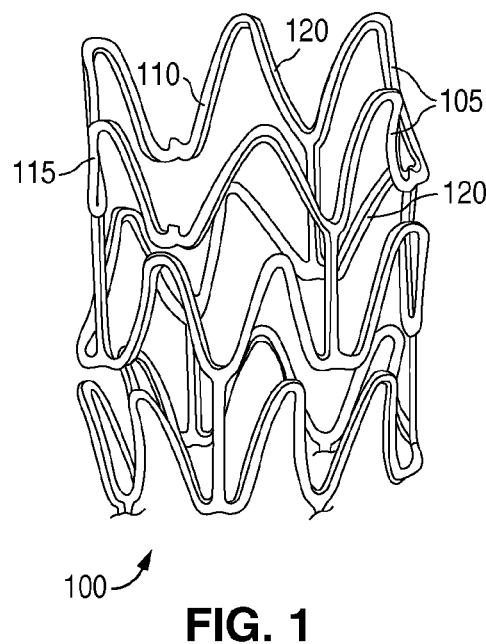
FIG. 1 depicts a view of a stent.

FIG. 1 depicts a view of a stent 100. In some embodiments, a stent may include a pattern or network of interconnecting structural elements or struts 105. Stent 100 may be formed from a tube (not shown). Struts 105 of stent 100 include luminal faces or surfaces 110, abluminal faces or surfaces 115, and side-wall faces or surfaces 120.

The present invention is not limited to the stent pattern depicted in FIG. 1. The pattern of structural elements 105 can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a stent pattern on the tube with a technique such as laser cutting or chemical etching. In an exemplary embodiment, the tube can be cut with a femtosecond laser.

A stent can be made partially or completely from a biodegradable, bioabsorbable, biostable polymer, or a combination thereof. A polymer for use in fabricating a stent can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

As a bioabsorbable stent degrades, its mechanical properties degrade. A bioabsorbable stent may be configured to disintegrate and disappear from the region of implantation once treatment is completed. The duration of a treatment period depends on the bodily disorder that is being treated. For illustrative purposes only, in treatment of coronary heart disease involving use of stents in diseased vessels, the duration can be in a range from about a month to a few years. However, the duration is typically in a range from about six to twelve months. Thus, it is desirable for polymer-based coatings and substrates of a stent to have a degradation time at or near the duration of treatment. Degradation time refers to the time for stent to substantially or completely erode away from an implant site.

One difficulty presented by stenting is new intimal growth, neointima, that forms after stenting which resides between the Internal Elastic Lamina and the vessel lumen. Another problem is inflammation of vascular tissue caused by the presence of the stent. Bioabsorbable polymeric stents, in particular, can trigger acute or chronic inflammatory responses due to the degradation of the stent. The vascular response to a fully bioabsorbable stent can be much different than that of a metal or polymer coated stent. Additionally, the re-endothelialization of the arterial lumen is critical for the healing response of the vessel. Without a healthy endothelium, the red blood cells will be prone to activation leading to thrombi.

Embodiments of the stent of the present invention provide therapies for facilitating re-endothelialization of arterial lumen to promote healing of the vascular tissue. In addition, the stent can further include therapies for reducing or preventing neointimal growth and inflammation of vascular tissue.

Certain embodiments of the present invention include a stent including a prohealing material. The stent can be made in whole or in part of a bioabsorbable polymer. The prohealing material can be dispersed within the bioabsorbable polymer. A prohealing material refers to a material that has the property that it promotes or enhances re-endothelilialization of arterial lumen to promote healing of the vascular tissue. The prohealing-containing portions of the stent can attract, bind and eventually become encapsulated by endothelial cells. In certain embodiments, the prohealing-containing portions of the stent attract, bind, and become encapsulated by endothelial progenitor cells. The attraction, binding, and encapsulation of the cells will reduce or prevent the formation of emboli or thrombi due to the loss of the mechanical properties that could occur if the stent was insufficiently encapsulated. In some embodiments, the enhanced re-endothelialization promotes the endothelilialization at a rate faster than the loss of mechanical properties of the stent.

In some embodiments, the prohealing material can be dispersed in the body of the bioabsorbable polymer substrate or scaffolding. The prohealing material can also be dispersed within a bioabsorbable polymer coating over a surface of a stent.

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing material can be an endothelial cell (EDC) binding agent. In some embodiments, the EDC binding agent can be protein, peptide and antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways (see, e.g., Martin, S. M., et al., J. Biomed. Mater. Res. 70A:10-19 (2004)). Endothelial cells can be selectively targeted (for the targeted delivery of immunoliposomes) using scFv A5 (Volkel, T., et al., Biochimica et Biophysica Acta 1663:158-166 (2004)). Junction membrane protein vascular endothelial (VE)-cadherin has been shown to bind to endothelial cells and down regulate apoptosis of the endothelial cells (Spagnuolo, R., et al., Blood 103:3005-3012 (2004)).

In some embodiments, the EDC binding agent can be the active fragment of osteopontin, (Asp-Val-Asp-Val-Pro-Asp-Gly-Asp-Ser-Leu-Ala-Try-Gly). Other useful EDC binding agents include EPC (epithelial cell) antibodies, RGD peptide sequences, RGD mimetics, and combinations thereof.

The EDC binding protein and peptide can be prepared according to the established methods, e.g., isolation and purification from natural sources, recombinant techniques, or combinatorial chemistry for the synthesis of peptides. For example, the active fragment of osteopontin can be readily prepared by combinatorial synthesis using, e.g., solid-phase peptide sequencing (e.g., a Merrifield synthesis). The scFv A5 protein can be synthesized by gene expression as described in the literature from the HisCysForNot(5'-TAG TGC GGC CGC TTA GCA TGC TCC GCC ATG GTG ATG GTG ATG ATG CGC ACG TTT GAT TTC CAG TTT GGT-3') (Volkel, T., et al., Biochimica et Biophysica Acta 1663: 158-166 (2004)).

In further embodiments, the prohealing material may be a substance or agent that attracts and binds endothelial progenitor cells. Representative substances or agents that attract and bind endothelial progenitor cells include antibodies such as CD-34, CD-133, and vegf type 2 receptor. An agent that attracts and binds endothelial progenitor cells can include a polymer having nitric oxide donor groups.

In other embodiments, the EDC binding agent can be chemically linked to a polymer (e.g., via a linkage). The polymer can be the polymer of the coating or a polymer from which the device is made. For example, the active fragment of osteopontin can be attached to the acid terminal poly(lactic acid) via a PEG linkage.

In some embodiments, a stent can include a prohealing material and one or more active agents for treating vascular disorders including, but not limited to, inflammation, neointimal proliferation, or both. In certain embodiments, the prohealing material can promote rapid endothelialization on a luminal side of the stent and treat inflammation and neointimal proliferation on the abluminal side of the stent. In such embodiments, a stent can include a prohealing layer and a drug-polymer layer above a luminal surface of the prohealing layer. In one embodiment, the prohealing layer can make up a majority of the body of the stent body. In a particular embodiment, the stent can have a plurality of structural elements or struts, the struts being composed of abluminal layers, luminal layers, and inner layers between the abluminal and luminal layers.

In some embodiments, the prohealing layer can include a prohealing material mixed, dispersed, or blended within a bioabsorbable polymer matrix. The prohealing layer can have at least 0.01, 0.1, 1, 2, 5, or at least 10 wt % of the prohealing material. In exemplary embodiments, the bioabsorbable polymer of the matrix can be poly(ester amide) (PEA), poly (L-lactide) (PLLA), poly(DL-lactide), polycaprolactone, polyglycolide, or copolymers or blends thereof. In further embodiments, the stent body can also include a luminal or base polymer layer on a luminal surface of the prohealing layer. The base polymer layer can be a bioabsorbable polymer that is the same or different polymer than the matrix polymer of the prohealing layer. As described in more detail below, the prohealing layer can be formed in a coating process over a polymer tube composed of the base polymer.

Additionally, the drug-polymer layer can include a drug or active agent mixed or dispersed in a bioabsorbable polymer matrix. The bioabsorbable polymer of the matrix can be the same or a different from the matrix polymer from the prohealing layer. The active agent can include anti-proliferative agents, anti-inflammatory agents, other agents, or a combination thereof. An exemplary anti-proliferative agent is everolimus.

In further embodiments, one or more additional luminal drug-polymer layers can be included on a luminal side of the stent. Alternatively, an additional drug-polymer layer can be over the luminal surface, abluminal surface, and sidewall surfaces of the struts of a stent. Such additional layers can include anti-thrombotic agents, vasodilators, or a combination thereof. Vasodilators refer to agents that act as blood vessel dilators and open vessels by relaxing their muscular walls.

Exemplary types of anti-thrombotic drugs include anti-platelet drugs and anticoagulant drugs. Exemplary anti-platelet drugs include acetylsalicylic acid, dipyridamole, ticlopidine, abciximag, and GP IIb/IIIa Inhibitors. Exemplary types of anticoagulant drugs include heparin, low molecular weight heparin, warfarin, and direct thrombin inhibitors. Exemplary vasodilators or calcium channel blockers include verapamil, diltiazem, and dihydropyridines (e.g., amlodipine, relodipine, isradipine, nicardipine, nifedipine, nisoldipine).

Figure 2:
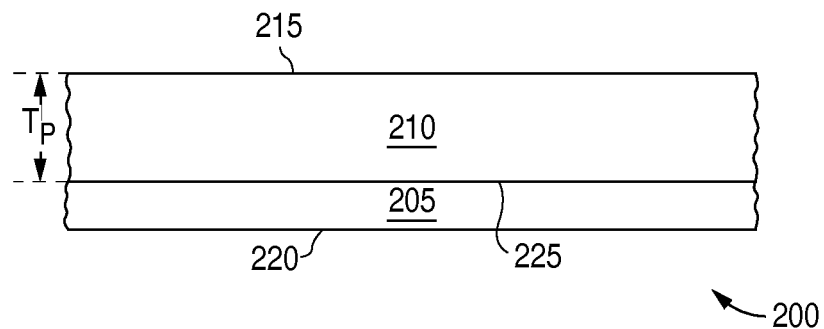
FIG. 2 depicts an exemplary embodiment a strut with an endothelial cell progenitor layer.

FIG. 2 depicts a sidewall of an exemplary embodiment of a strut 200. Strut 200 has a prohealing layer 210 as an abluminal layer with an abluminal surface 215. Prohealing layer 210 is composed of prohealing material (not shown) mixed or dispersed within a bioabsorable polymer. Prohealing layer 210 is over a luminal base polymer layer 205 with a luminal surface 220.

Figure 3:
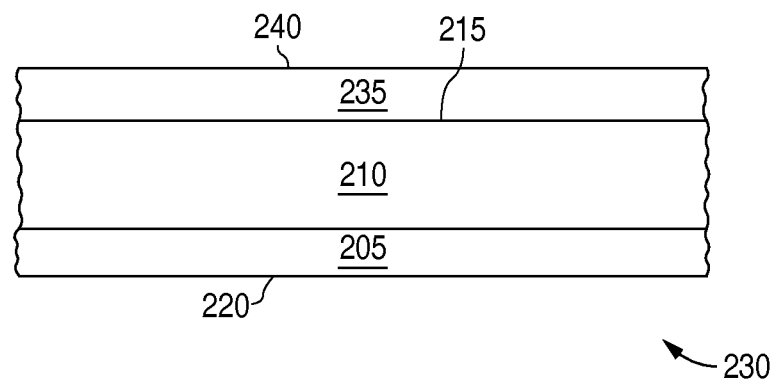
FIG. 3 depicts an exemplary embodiment a strut with an endothelial cell progenitor layer and a drug-polymer layer.

FIG. 3 is another exemplary embodiment showing a strut 230. Strut 230 is the same strut 200 of FIG. 2 except that strut 230 includes a drug-polymer layer 235 over prohealing layer 210. Drug-polymer layer 235 has a luminal surface 240. Drug-polymer layer 235 can include an anti-proliferative drug, anti-inflammatory drug, or both for treatment of inflammation in a vascular wall and/or neointimal proliferation. The drug in drug-polymer layer 235 can be mixed or dispersed within a bioabsorbable polymer.

Figure 4:
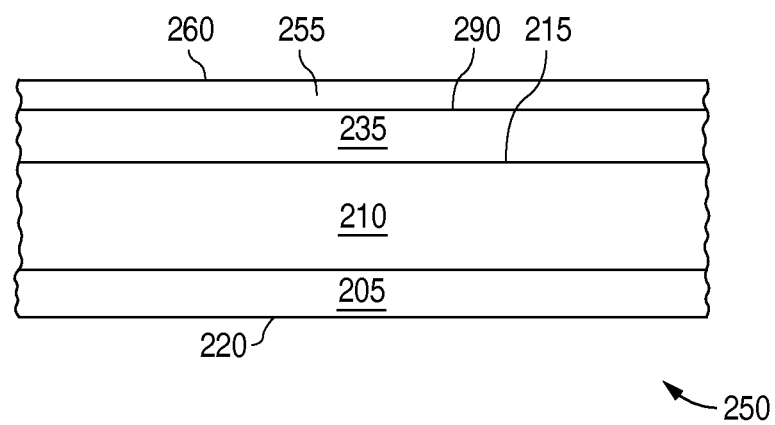
FIG. 4 depicts an exemplary embodiment a strut with an endothelial cell progenitor layer and two drug-polymer layers.

FIG. 4 depicts an additional exemplary embodiment showing strut 250 which is the same as strut 230 of FIG. 3 except that strut 250 includes a second drug-polymer layer 255 that has a luminal surface 250. Second drug-polymer layer 255 can have an anti-thrombotic agent or a vasodilator mixed or dispersed within a bioabsorbable polymer.

Figure 5:
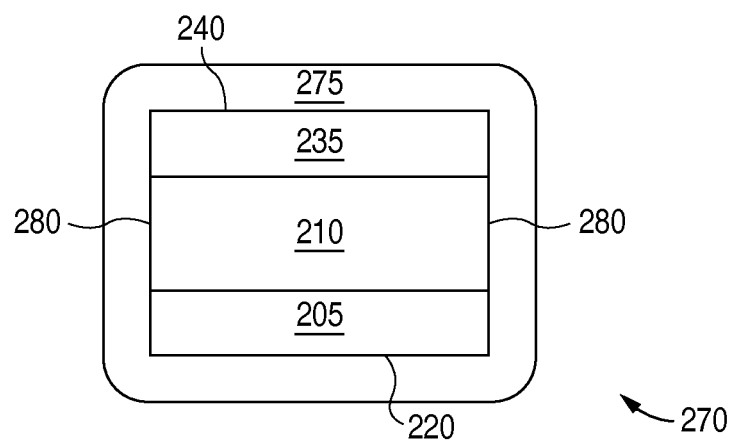
FIG. 5 depicts an alternative to FIG. 4 with a drug-polymer coating layer around the luminal, abluminal, and sidewall surfaces of a strut.

FIG. 5 depicts an alternative embodiment to that shown in FIG. 4. An axial cross-section of a strut 270 is shown. Second drug-polymer layer 275 is disposed over luminal surface 220, abluminal surface 240, and sidewall surfaces 280.

In one embodiment, prohealing layer 210 can be large enough that it provides most or all of the mechanical support for wall of a bodily lumen. A thickness Tp of prohealing layer 210 can be large enough that it has sufficient radial strength to support such bodily lumen. In exemplary embodiments, thickness Tp of prohealing layer 210 can be two thirds to three fourths of the total thickness of a strut. In such embodiments, the total strut thickness can be 0.003"-0.0035."

Upon implantation of a stent with struts 200, 230, or 250, base polymer layer 205 can erode away, exposing luminal surface 225 of prohealing layer 210. As prohealing layer 210 degrades and is absorbed, prohealing material enhances endothelialization which promotes healing of the vessel. The enhancement of endothelialization occurs throughout the absorption of prohealing layer 210. As indicated above, in some embodiments, a majority of the thickness of the stent body can be a prohealing layer and such layers can account for most or all of the structural support. Thus, in such embodiments, the prohealing effect of the stent can occur during most of the time period of degradation of the stent.

In addition to the prohealing, an implanted stent with struts 230 can also treat inflammation, neointimal proliferation, or both at an abluminal layer of the stent. Furthermore, an implanted stent with struts 250 and 270 with an anti-thrombotic agent can reduce or eliminate the occurrence of thrombosis at or near the implant site. Struts 250 and 270 with a vasodilator can facilitate dilation of the vessel at or near the implant site.

Further embodiments of the present invention include a method of fabricating a bioabsorbable stent having a prohealing layer. In some embodiments, a prohealing layer can be formed by forming a prohealing coating over a polymer tube. A laser can then be used to cut a stent pattern in the tube to form a stent. The polymer tube corresponds to the base polymer layer 205 shown in FIGS. 2-5. The polymer tube can be made of a bioabsorbable polymer. The polymer tube can be formed through extrusion.

A prohealing layer is formed by applying a coating material to the polymer tube. The tube can be formed by extrusion or injection molding. Alternatively, a polymer sheet can be rolled and bonded to form a tube. The coating material includes a bioabsorbable polymer dissolved in a suitable solvent. The coating material also includes a prohealing material mixed, dispersed, or dissolved in the solvent. In some embodiments, the prohealing material can be the bioabsorbable polymer, be bonded to the bioabsorbable polymer, or be another bioabsorbable polymer. The solution can than be sprayed on a stent using methods know to those of skill in the art. Alternatively, the stent can be dipped in the coating material solution. The coating can then be dried or cured to remove the solvent. The stent can be air dried or dried in an oven. The spraying or dipping/drying can be repeated a number of times to obtain a desired thickness of the prohealing layer.

Additionally, a drug-polymer layer can be formed in a similar manner over the prohealing layer and over other drug-polymer layers. For example, a drug-polymer coating material can be applied over the prohealing layer or another drug-polymer layer. The coating material can include a bioabsorbable polymer layer dissolved in a suitable solvent. The coating material can be applied by spraying or dipping and then dried. The spraying or dipping/drying can be repeated a number of times to obtain a desired thickness of the drug-polymer layer.

Figure 6:
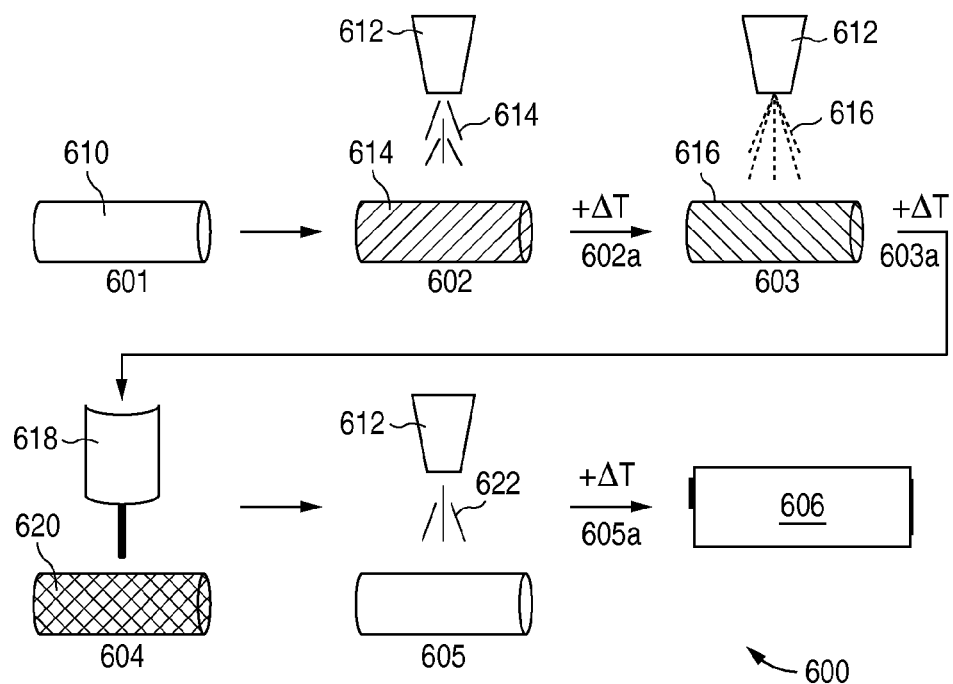
FIG. 6 depicts a process flowchart illustrating the fabrication of an exemplary stent as depicted in FIG. 4 or 5

A stent can be fabricated from the coated tube by laser machining a pattern in to the tube. FIG. 6 depicts a process flowchart 600 illustrating the fabrication of an exemplary stent as depicted in FIG. 4 or 5. The process is as follows:

601 A polymer tube 610 (e.g., PEA, PLLA) is fabricated by extrusion or injection molding.

602 Spray coat tube 610 using a nozzle 612 with coating material 614 including bioabsorbable coating polymer (e.g., PEA, PLLA) and prohealing material.

602a Dry or cure coating.

603 Spray coat tube 610 using a nozzle 612 with a coating material 616 including bioabsorbable coating polymer and anti-proliferative drug (e.g., everolimus) and/or an anti-inflammatory drug.

603a Dry or cure coating.

604 A laser 618 is used to cut a stent pattern from the coated tube of step 603 to form a stent 620.

605 Spray coat stent 620 using a nozzle 612 with coating material 622 including bioabsorbable coating polymer and an anti-thrombotic drug or vasodilator.

605a Dry or cure coating.

606 Post-processing (e.g., packaging, sterilization).

In alternative embodiments, a stent pattern can be formed from uncoated tube at step 601, from the coated tube after step 602a, or from the coated tube after step 603a. The layers of the cut tube can then be applied by selectively applying coating material to the luminal surface of the struts.

With respect to the alternative embodiments of forming the stent, various methods may be used to form abluminal coatings including, but not limited to, ink-jet-type coating, electrostatic coating, roll coating, thermal deposition with masking, plasma polymerization with masking, direct application of polymer/solvent solution by micro-syringe, direct polymer melt application, and spray coating with photomasking. For example, a controlled deposition system ink jet-type coating method can be used that applies various substances only to certain targeted portions of a stent. A representative example of such a system, and a method of using the same, is described in U.S. Pat. No. 6,395,326 to Castro et al. A controlled deposition system can be capable of depositing a substance on stent having a complex geometry, and otherwise apply the substance so that coating is limited to particular portions of the stent, such as an abluminal surface of struts. The system can have a dispenser and a holder that supports the stent. The dispenser and/or holder can be capable of moving in very small intervals, for example, less than about 0.001 inch. Furthermore, the dispenser and/or holder can be capable of moving in the x-, y-, or z-direction, and be capable of rotating about a single point.

The controlled deposition system can include a dispenser assembly. The dispenser assembly can be a simple device including a reservoir, which holds a coating material prior to delivery, and a nozzle having an orifice through which the coating material is delivered. One exemplary type of dispenser assembly can be an assembly that includes an ink-jet-type printhead. Another exemplary type of a dispenser assembly can be a microinjector capable of injecting small volumes ranging from about 2 to about 70 nL, such as NanoLiter 2000 available from World Precision Instruments or Pneumatic PicoPumps PV830 with Micropipette available from Cell Technology System. Such microinjection syringes may be employed in conjunction with a microscope of suitable design.

Furthermore, selective coating of surfaces of a stent may be performed using photomasking techniques. Deposition and removal of a mask can be used to selectively coat surfaces of substrates. Masking deposition is known to one having ordinary skill in the art.

Additionally, the coating materials of the present invention can also be selectively deposited by an electrostatic deposition process. Such a process can produce an electrically charged or ionized coating material. The electric charge causes the coating material to be differentially attracted to the stent, thereby resulting in higher transfer efficiency. The electrically charged coating material can be deposited onto selected regions of the stent by causing different regions of the device to have different electrical potentials.

In general, representative examples of polymers that may be used in embodiments of the present invention include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

As indicated above, drugs or therapeutic active agent(s) can include anti-inflammatories, antiproliferatives, and other bioactive agents.

An antiproliferative agent can be a natural proteineous agent such as a cytotoxin or a synthetic molecule. The active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammmatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic anti-thrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable. For the purposes of the present invention, the following terms and definitions apply:

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:
   a bioabsorbable prohealing layer configured to promote endothelialization upon exposure to bodily fluids,
   wherein the prohealing layer comprises an endothelial cell (EDC) binding agent that attracts and binds endothelial cells,
   wherein the substance is dispersed within a bioabsorbable polymer matrix,
   wherein a bioabsorbable polymer of the matrix is poly(L-lactide), polyglycolide, poly(ester amide), or poly(L-lactide-co-glycolide); and
   a bioabsorbable drug-polymer layer on an abluminal surface of the prohealing layer,
   wherein the drug-polymer layer comprises a drug mixed or dispersed within a bioabsorbable polymer that is the same as the bioabsorbable polymer of the matrix,
   wherein the stent is completely bioabsorbable and upon implantation in a vessel is configured to completely erode and disappear from the vessel.

2. The stent of claim 1, wherein the EDC binding agent comprises a protein, peptide, or antibody.

3. The stent of claim 1, wherein the EDC binding agent is an active fragment of osteopontin.

4. The stent of claim 1, wherein the EDC binding agent is selected from the group consisting of epithelial cell antibodies, RGD peptide sequences, RGD mimetics, and combinations thereof.

5. The stent of claim 1, wherein the drug-polymer layer comprises an active agent selected from the group consisting of anti-proliferative agents, anti-inflammatory agents and combinations thereof.

6. The stent of claim 1, further comprising a bioabsorbable polymeric base layer over a luminal surface of the prohealing layer, wherein the bioabsorbable polymeric base layer is a bioabsorbable polymer that is the same as the bioabsorbable polymer of the matrix.

7. The stent of claim 6, further comprising a coating on a luminal surface of the base layer, wherein the coating comprises heparin.

8. A method of fabricating a bioabsorbable stent, the method comprising:
   forming a bioabsorbable prohealing coating layer over a bioabsorbable base polymer tube, the prohealing coating layer configured to promote endothelialization upon exposure to bodily fluids,
   wherein the prohealing layer comprises an endothelial cell (EDC) binding agent that attracts and binds endothelial cells,
   wherein the substance is dispersed within a bioabsorbable polymer matrix,
   wherein a bioabsorbable polymer of the matrix is poly(L-lactide), polyglycolide, or poly(L-lactide-co-glycolide),
   wherein the bioabsorbable base polymer tube is a bioabsorbable polymer that is the same as the bioabsorbable polymer of the matrix; and
   forming a bioabsorbable drug-polymer layer over the prohealing coating layer; and
   laser cutting a stent pattern in the coated polymer tube to form a stent,
   wherein the stent is completely bioabsorbable upon implantation in a vessel.

9. The method of claim 8, further comprising forming a top-coat layer over the drug-polymer layer.

10. The method of claim 9, wherein the top-coat layer comprises an anti-thrombotic drug or vasodilator dispersed in a bioabsorbable polymer.

11. The method of claim 8, wherein the EDC binding agent comprises a protein, peptide, or antibody.

12. The method of claim 8, wherein the EDC binding agent is an active fragment of osteopontin.

13. The method of claim 8, wherein the EDC binding agent is selected from the group consisting of epithelial cell antibodies, RGD peptide sequences, RGD mimetics, and combinations thereof.

14. The method of claim 8, wherein the drug-polymer layer comprises a drug mixed or dispersed within a bioabsorbable polymer that is the same as the bioabsorbable polymer of the matrix, wherein the drug is selected from the group consisting of anti-proliferative agents, anti-inflammatory agents and combinations thereof.

15. The method of claim 8, wherein the prohealing coating layer is formed by applying a coating material comprising the substance and the bioabsorbable polymer of the matrix dissolved in a solvent and removing the solvent.

16. The method of claim 8, wherein the drug-polymer layer is formed by applying a coating material comprising a drug and a dissolved bioabsorbable polymer that is the same as the bioabsorbable polymer as the matrix in a solvent and removing the solvent.

\* \* \* \* \*